US00PP12200P2

(12) United States Plant Patent
Zary

(10) Patent No.: US PP12,200 P2
(45) Date of Patent: Nov. 13, 2001

(54) HYBRID TEA ROSE PLANT NAMED 'JACLADIN'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/455,227

(22) Filed: Dec. 6, 1999

(51) Int. Cl.[7] ..... A01H 5/00
(52) U.S. Cl. ..... Plt./139

(58) Field of Search ..... Plt./139, 140

(56) References Cited

U.S. PATENT DOCUMENTS

P.P. 5,519 * 7/1985 McGredy, IV ..... Plt./139

* cited by examiner

*Primary Examiner*—Howard J. Locker
(74) *Attorney, Agent, or Firm*—Klarquist Sparkman, LLP

(57) ABSTRACT

A hybrid tea rose plant having bright red flowers with heavy petal substance on long stems; vigorous, upright growth; and glossy, disease resistant foliage.

1 Drawing Sheet

The present invention relates to a new and distinct variety of rose plant of the hybrid tea class which was originated by me by crossing the variety MACauck (U.S. Plant Pat. No. 5,519), with the variety POULman (U.S. Plant Pat. No. 6,264).

The primary objective of this breeding was to produce a new rose variety having the long stems, excellent vigor and bright red flower color of the female parent, combined with the very glossy foliage, heavy petal substance and resistance to disease of the male parent. The objective was substantially achieved, along with other desirable improvements, as evidenced by the following unique combination of characteristics that are outstanding in the new variety and that distinguish it from its parents, as well as from all other varieties of which I am aware:

1. Long cutting stems;
2. Heavy petal substance;
3. Glossy foliage;
4. Vigorous, upright growth;
5. Disease resistant foliage; and
6. Bright red flower color.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent*.—MACauck (U.S. Plant Pat. No. 5,519).
*Pollen parent*.—POULman (U.S. Plant Pat. No. 6,264).

Classification:

*Botanical*.—*Rosa hybrida*.
*Commercial*.—Hybrid tea.

FLOWER

Observations made from specimens grown in a garden environment at Somis, Calif. from Mar. 1998 to Aug. 1999.

Blooming habit: Continuous.

Bud:

*Size*.—About 1½ inches long when the petals start to unfurl.
*Form*.—The bud form is long; pointed ovoid.
*Color*.—When sepals first divide, bud color is Red Group 45A with some of the petal edge on the guard petals blackened. When half blown, the upper sides of the petals are Red Group 45B; and the lower sides of the petals are Red Group 45B.
*Sepals*.—Color: Green Group 138B with some areas of Greyed-Purple Group 183D when exposed to bright sunlight. Surface texture: Covered in fine hairs. There are three normally appendaged sepals. There are two unappendaged sepals with hairy edges.
*Receptacle*.—Color: Green Group 137A but often, when in bright sunlight, Greyed-Purple Group 183A. Shape: Funnel. Size: Medium (about ⅜×2/16 inches). Surface: Smooth.
*Peduncle*.—Length: Medium (about 2½ to 3 inches). Surface: Smooth. Color: Green Group 137A but often, when exposed to bright sunlight, Greyed-Purple Group 183A. Strength: Stiff; erect.

Bloom:

*Size*.—Large. Average open size is 4½ to 5 inches.
*Borne*.—Singly.
*Stems*.—Strength: Strong. Average length is about 18 to 22 inches.
*Form*.—When first open: High centered. Permanence: Flattens; all petals curl quill fashion.
*Petalage*.—Number of petals under normal conditions: 30.

*Color*.—The upper sides of the petals are Red Group 45B. The reverse sides of the petals are Red Group 45B. The base of each petal has on the upper surface a 3/16 inch×3/16 inch, Yellow Group 7D half moon at the point of attachment. The lower surface has a 1/8 inch×1/8 inch, Yellow Group 8C half moon at the point of attachment. The major color on the upper sides is Red Group 45B.

*Variegations*.—None.

*Discoloration*.—The general tonality at the end of the first day: No change. At the end of the third day: No change. By day six or seven, petal drop has occurred in the field. Just prior to petal drop, there is a color degredation to Red Group 53C.

*Fragrance*.—None.

Petals:

*Texture*.—Thick.

*Shape*.—Round.

*Form*.—Tips slightly recurved; edges slightly quilled.

*Arrangement*.—Imbricated. No petaloids in the center.

*Persistence*.—Petals drop off cleanly before drying.

*Lastingness*.—On the plant: Fair (about six or seven days). As a cut flower: Fair (about seven or eight days).

Reproductive parts:

*Anthers*.—Size: Medium. Quantity: Many. Color: Yellow-Orange Group 22C. Arrangement: Regular around styles.

*Filaments*.—Color: Red Group 53A.

*Pollen*.—Present.

*Styles*.—Color: Red Group 53B.

Plant:

*Form*.—Bush.

*Growth*.—Vigorous; upright; branching. At maturity, height is five feet, width is 3½ feet.

Foliage: Number of leaflets on normal mid-stem leaves: Five or seven.

*Size*.—Large (6½ to 7 inches long×5 inches wide).

*Quantity*.—Abundant.

*Color*.—New foliage: Upper and lower surfaces: Greyed-Red Group 178A. Old foliage: Upper surface: Green Group 131A. Lower surface: Green Group 139C.

Leaflets:

*Shape*.—Pointed oval.

*Texture*.—Leathery; glossy.

*Edge*.—Serrated.

*Serration*.—Single; small.

*Petiole rachis*.—Color: Upper: Green Group 137B. Lower: Green Group 137D.

*Petiole underside*.—Smooth; with occasional prickles.

*Stipules*.—Medium (about 5/8 inch to 3/4 inch long); serrated; bearded.

*Disease resistance*.—Resistant to mildew and rust; susceptible to blackspot under normal growing conditions.

Wood:

*New wood*.—Color: Greyed-Purple Group 183A. Bark: Smooth.

*Old wood*.—Color: Green Group 139A. Bark: Smooth.

Prickles:

*Quantity*.—On main canes from base: Ordinary. On laterals from main canes: Ordinary.

*Form*.—Medium; hooked downward.

*Color when young*.—Greyed-Purple Group 183B.

*Color when mature*.—Greyed-Orange Group 179C.

Small prickles:

*Quantity*.—On main stalks: None. On laterals: None.

I claim:

1. A new and distinct variety of rose plant of the hybrid tea class, substantially as herein shown and described, characterized particularly by having bright red flowers having heavy petal substance on long stems; vigorous, upright growth; and glossy, disease resistant foliage.

* * * * *

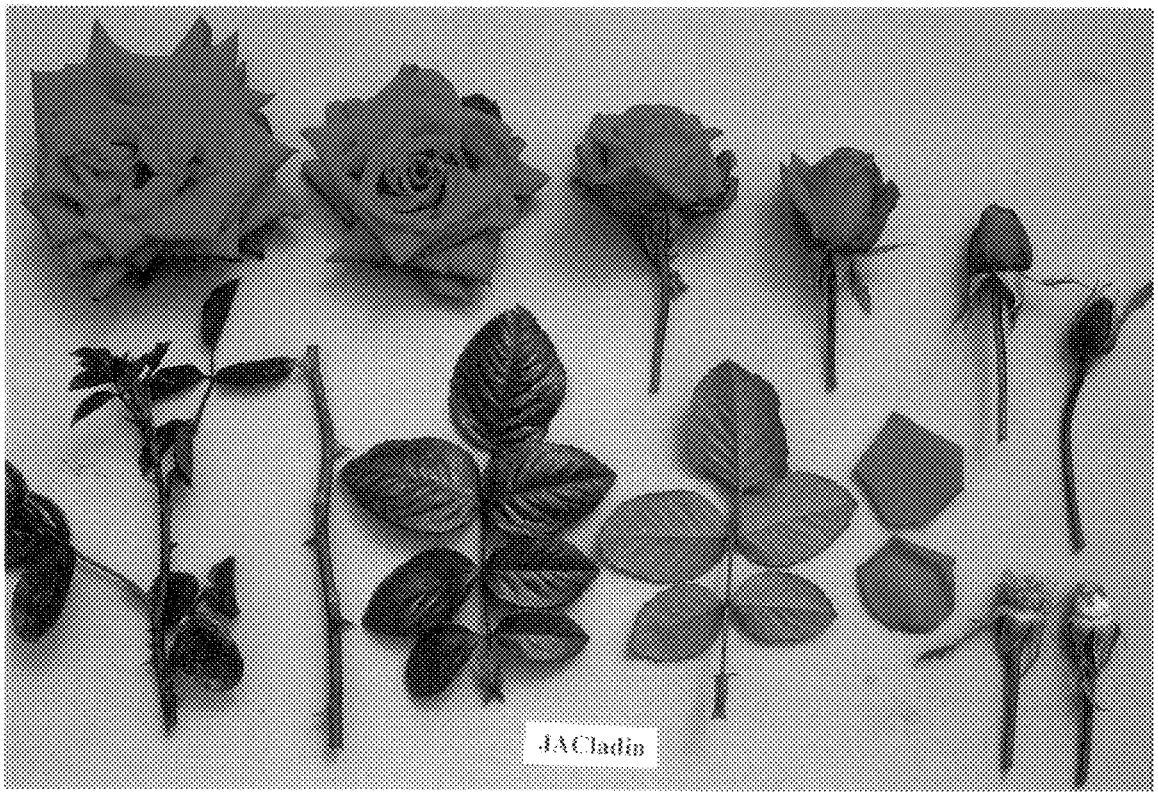
JACladin